United States Patent [19]

Barcza

[11] 4,434,161
[45] Feb. 28, 1984

[54] SULFUR AND SILICON-CONTAINING FATTY ACID AMIDES

[75] Inventor: Sandor Barcza, Mt. Lakes, N.J.

[73] Assignee: Sandoz, Inc., East Hanover, N.J.

[21] Appl. No.: 427,606

[22] Filed: Sep. 29, 1982

[51] Int. Cl.$^3$ .............................................. C07F 7/10
[52] U.S. Cl. .................................... 424/184; 556/419; 548/406
[58] Field of Search ....................... 556/419; 424/184; 548/406

[56] References Cited

U.S. PATENT DOCUMENTS

| | | | |
|---|---|---|---|
| 3,660,454 | 5/1972 | Gornowicz et al. | 556/419 X |
| 3,812,164 | 5/1974 | Schulz | 556/419 X |
| 4,297,349 | 10/1981 | Barcza | 556/419 X |
| 4,328,216 | 5/1982 | Toyoshima et al. | 556/419 X |

OTHER PUBLICATIONS

"Artery", 5, No. 3, pp. 222–236, (1979).
"Experimental and Molecular Pathology", 18, pp. 162–176, (1973).
"Science", 180, pp. 1332–1339, (1973).

Primary Examiner—Paul F. Shaver
Attorney, Agent, or Firm—Gerald D. Sharkin; Richard E. Vila; Frederick H. Weinfeldt

[57] ABSTRACT

Sulfur and silicon-containing amides, e.g. N-5-sila-3-thia-5,5-dimethyl-pentadecanoyl-1-phenyl-2-(4-methylphenyl)-ethylamine, are useful as anti-atherosclerotic agents. The amides are obtainable by acylation of a primary amine (the substituents on the amine being of the aralkyl phenyl, tryptophanyl, benzocycloalkyl-type) with a corresponding sulfur and silicon-containing carboxylic acid (or active form thereof).

15 Claims, No Drawings

SULFUR AND SILICON-CONTAINING FATTY ACID AMIDES

This invention relates to organic compounds and more particularly to sulfur and silicon-containing fatty acid amides and to pharmaceutical compositions containing such compounds, as well as to the pharmaceutical use of such compounds.

The compounds of this invention are conveniently represented by the formula I:

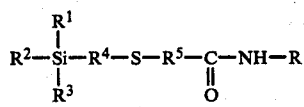     I wherein each of $R^1$, $R^2$ and $R^3$ is, independently, alkyl having from 1 to 22 carbon atoms, alkenyl having from 2 to 22 carbon atoms, cycloalkyl having from 3 to 20 ring carbon atoms, aryl having from 6 to 14 aromatic ring carbon atoms, or aralkyl having from 6 to 14 aromatic ring carbon atoms and from 1 to 4 carbon atoms in the alkylene portion thereof; or $R^2$ and $R^3$ may be joined to form together with the silicon atom a saturated sila-hydrocarbyl ring having from 4 to 20 ring members, provided that the total number of carbon atoms in $R^1 + R^2 + R^3$, other than aromatic ring carbon atoms or substituents thereon, is not more than 35, each of $R^4$ and $R^5$ is, independently, an alkylene chain having from 1 to 6 carbon atoms, or a cycloalkylene radical having from 3 to 6 ring carbon atoms, said cycloalkyl and cycloalkylene radicals may bear from 1 to 4 lower alkyl groups having from 1 to 6 carbon atoms; said aryl radicals, or portions thereof, may bear 1 or 2 halo substituents, each having an atomic weight of from about 19 to 80, i.e. fluoro, chloro or bromo, or from 1 to 3 lower alkyl or alkoxy radicals each having from 1 to 6 carbon atoms; and R is of type (a) an aralkyl-type radical of the structure:

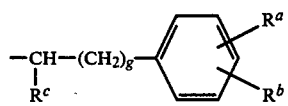     (a)

wherein
g is 0, 1 or 2;

$R^a$ is a hydrogen atom, halo having an atomic weight of from about 19 to 127, alkoxy having from 1 to 4 carbon atoms, or alkyl having from 1 to 4 carbon atoms, or trifluoromethyl;

$R^b$ is a hydrogen atom, alkyl having from 1 to 3 carbon atoms, alkoxy having from 1 to 3 carbon atoms, or halo having an atomic weight of from about 19 to 36; and $R^c$ is subtype (i) a hydrogen atom; subtype (ii) a radical of the structure

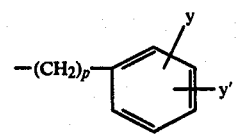     (ii)

in which p is 0, 1 or 2, and y is a hydrogen atom, also having an atomic weight of from about 19 to 127, alkoxy having from 1 to 4 carbon atoms, or alkyl having from 1 to 4 carbon atoms; and y' is a hydrogen atom, alkoxy having from 1 to 3 carbon atoms, alkyl having from 1 to 3 carbon atoms, or halo having an atomic weight of from about 19 to 36; or subtype (iii) alkyl having from 1 to 8 carbon atoms; or R is of type (b) a phenyl-type radical of the structure

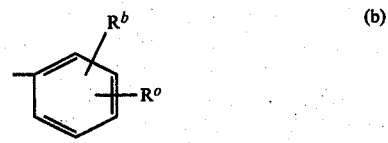     (b)

in which $R^b$ is as defined above, and $R^o$ is a hydrogen atom, halo having an atomic weight of from about 19 to 127, alkoxy having from 1 to 4 carbon atoms, or alkyl having from 1 to 4 carbon atoms; or $R^o$ is a radical of the structure $R^f$:

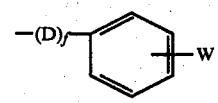

in which D is —CH$_2$— or —O—;

f is 0 or 1; and

W is a hydrogen atom, halo having an atomic weight of from about 19 to 80, alkoxy having from 1 to 3 carbon atoms, or alkyl having from 1 to 3 carbon atoms; or R is of type (c) an indolyl radical of the structure:

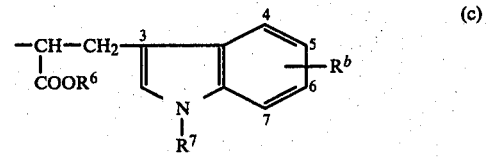     (c)

wherein $R^b$ is as defined above;

$R^6$ is alkyl having from 1 to 8 carbon atoms or benzyl; and $R^7$ is a hydrogen atom, alkyl having from 1 to 8 carbon atoms or benzyl; or R is (d) a benzocycloalkyl nucleus of the structure:

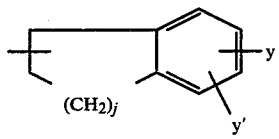

(d)

wherein
y and y' are is defined above; and
j is a whole integer of from 1 to 4.

With respect to the above-presented definitions of $R^1$ to $R^5$, the alkyl, alkylene and alkenyl radicals and alkyl portions of alkoxy radicals, may be branched or unbranched. Preferably $R^1$ is a higher hydrocarbon having from about 8 to 12 carbon atoms especially n-decyl and each of $R^2$ and $R^3$ is lower alkyl having from 1 to 4 carbon atoms, preferably unbranched, e.g. methyl, and more preferably $R^2$ and $R^3$ are the same. Where a moiety or radical bears more than one substituent they may be the same or different. When any of $R^1$, $R^2$ and $R^3$ is aryl it is preferably phenyl, and when aralkyl, it is preferably phenyl (lower) alkyl; the alkyl portion preferably having from 1 to 3 carbon atoms, and especially 1 or 2. $R^4$ and $R^5$ are both preferably (lower) alkylene (of from 1 to 4 carbon atoms), especially methylene.

It will be noted that $R^2$ and $R^3$ may be especially joined to form a saturated acyclic hydrocarbon radical forming with the silicon atom a heterocyclic ring having at least 4 but not more than 20 ring members and together with ring substituents no more than 25 carbon atoms. Such hydrocarbon radical may be branched, typically by methyl or ethyl groups, particularly 1 or 2 methyl groups, but is conveniently unbranched and represented by a polymethylene chain, i.e. —$(CH_2)_n$— which together with the silicon atom forms a cyclic structure; n being from 3 to 19, preferably from 3 to 13, particularly 4 to 7 and especially 4 or 5.

Further preferred forms of Compounds I when R is of type (a) or (b) and $R^o$ is not $R^f$, are that it is preferred that when $R^a$, $R^o$ or y is other than a hydrogen atom and $R^b$ (or y') is a hydrogen atom, that $R^o$, or $R^a$, or y be located at the 4-position; and that when $R^b$ (or y') is also other than a hydrogen atom that $R^a$ and $R^o$ and $R^b$ (or y and y') are the same, and it is additionally preferred that they be located at the 2- and 4-positions of the phenyl ring. When R is of type (a) where g=1, and $R^c$ is of type (ii) where p=0, then R can be an α-(phenyl)-β-(p-methylphenyl)ethyl radical, and when $R^c$ is of type (ii) where p=1, then R can be an α-(benzyl)-phenylethyl radical, these radicals being also known as 1'-phenyl-2'-(p-methylphenyl)ethyl and 1'-benzyl-2'-phenylethyl, respectively.

With particular respect to the substituent $R^0$ when it is a radical $R^f$, it will be appreciated that when $D=CH_2$ and f=1, then the radical $R^f$ is of the benzyl type. When D=oxygen and f=1, then the radical $R^f$ is of the phenoxy-type. When f=zero, then the radical $R^f$ is of the phenyl-type. Hence, when R is of type (b), and $R^o$ is of type $R^f$ where f=zero, then R can be a biphenylyl radical. The radical $R^f$ is preferably at the para-position. When W is other than a hydrogen atom, it is preferably at the para-position.

With respect to R, when it is of type (c), it is preferred that when $R^b$ is other than a hydrogen atom, it be located at the 5-position of the indole nucleus. It is also preferred that when $R^6$ is alkyl, it is unbranched, particularly ethyl.

With respect to R when it is of type (d) it is preferred that when y is other than a hydrogen atom, that it be located at a carbon atom ortho to the ring junction; and that when y' is also other than a hydrogen, it is preferred that it be the same as y, and it is additionally preferred that it be in para-relationship to y'. It is additionally preferred that the amide group be linked to a carbon of the cycloalkyl moiety which is directly bonded to a ring junction carbon. It is also preferred that j be 1, i.e. that the benzocycloalkyl nucleus be indanyl, and particularly 1-indanyl.

In the above-presented definitions, when $R^0$, $R^a$ or y is halo, it is preferably fluoro or chloro, and particularly chloro; and when $R^b$ or y' is halo it is preferably chloro.

Compounds I of this invention may be obtained by reaction of a primary amine (ii) bearing the desired moiety-R as defined above with a compound III, i.e. a carboxylic acid (or derivative thereof) bearing the "acyl" portion of the desired Compound I. Such acylation may be carried out by conventional means employed in converting a primary amine function to its corresponding secondary amide, such as are reported in the literature.

The compounds of formula (I) may be prepared according to the following reaction scheme (process a):

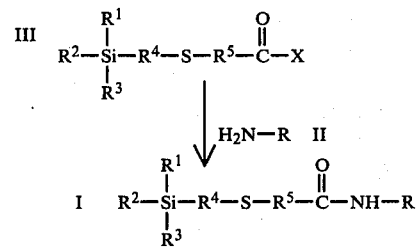

wherein R and $R^1$ to $R^5$ are as defined above, and X is hydroxy, alkoxy or aryloxy, or halo having an atomic weight of from about 35 to 80, i.e. chloro or bromo, a pseudo-halide, or III may be an "anhydride" or a "mixed anhydride", or the like as are well known in the art.

A particularly convenient method of preparing compounds I comprises reacting (process a1) an acyl halide of the formula IV

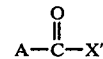

IV in which A is the moiety

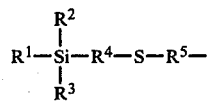

in which $R^1$ to $R^5$ are as defined above, and X' is either chloro or bromo, with a compound II (as defined above), in the presence of an acid acceptor e.g. an organic base, such as triethylamine or excess of compound II, in an inert medium at moderate temperatures, e.g. from about −50° to +50° C. preferably at about 0° to +30° C., in an inert medium e.g. a chlorinated hydrocarbon, such as dichloromethane, or an aromatic hydrocarbon, such as toluene.

The acyl halides (IV) may be prepared in the conventional manner, e.g. by treating (process b1) a corresponding compound III (as defined above), in which X is OH, i.e. a compound V, with a halogenating agent capable of contributing a chlorine or bromine atom, e.g. oxalyl chloride or thionyl chloride (or -bromide, as appropriate).

Similarly, the acylation (process a) may conveniently be carried out by a mixed anhydride technique (process a2) wherein a compound II is treated with a mixed anhydride of the formula III':

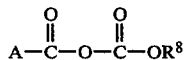
III' in which A is as defined above and $R^8$ is a lower alkyl having from 1 to 6 carbon atoms, at moderate temperatures, e.g. from about $-10°$ C. to $+35°$ C., in an inert organic medium, e.g. a chlorinated hydrocarbon, such as methylene chloride.

The mixed anhydrides (III') are obtainable by reacting (process b2) a free carboxylic acid of the formula V:

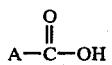
V wherein A is as defined above, with a chloroformate of the formula VI:

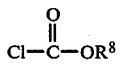
VI wherein $R^8$ is as defined above, in the presence of an acid acceptor, e.g. an organic base, such as triethylamine, at reduced temperatures, e.g. at from about $-10°$ to $+30°$ C., in an inert organic medium, e.g. a chlorinated hydrocarbon, such as methylene chloride.

In the above-described processes, neither the media nor the temperature are critical to the reactions, and where the reactants or reagents are liquid, an excess thereof may serve as the reaction medium. If desired a compound II may be in the form of an acid addition salt, for example the hydrochloride. The mixed anhydride (III') resulting from process b2 may conveniently be used in situ. That is to say that provided that the materials in the reaction mixture containing the mixed anhydride are not detrimental, they may be used directly for process a2) without recovery.

Compounds III (the "acyl" contributing intermediates) may be obtained by adapting appropriate known techniques; some compounds III being known, e.g. where $R^1=R^2=R^3=$methyl reported in Chem. Abst. 90, 39029z.

A convenient method of preparing compounds V is by reacting a corresponding leaving group-bearing-silane of the formula VII:

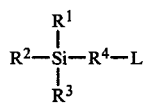
VII in which $R^1$ to $R^4$ are as defined above, and L is a leaving group such as a halo, i.e. chloro, bromo or iodo, preferably iodo, or an ester of an alkyl or aryl sulfonic acid, e.g. a p-toluene sulphonate, with a mercapto-fatty acid (or active derivative) of the formula VIII:

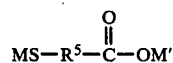
VIII $R^5$ is as defined above, and each of M and M' is a hydrogen atom or one equivalent of a cation, in an inert medium, preferably a polar solvent such as dimethylformamide, at moderate temperatures, e.g. at from 20° to 180° C., such as at the reflux temperature of the reaction mixture, generally under essentially anhydrous conditions. The cation is preferably metallic, especially of an alkali metal, such as sodium. If desired, M' may be a protecting group which can be removed later, or retained where OM' may serve as X. Where both M and M' are H, (or M' is protected) it is preferable to add a base, such as triethylamine.

Reagents and reactants described herein, e.g., compounds II, III, III', IV, V, VI, VII and VIII are known and obtainable by known means, or where not known, may be obtained by adaptation of methods reported in the literature for the preparation of known analogs; many such compounds being commercially available. For example, some Compounds VII are described in U.S. Pat. No. 4,297,349.

The final products and intermediate compounds described herein may be recovered and refined, where such is desired, by conventional means, such as by crystallization, distillation or chromatographic techniques such as column or thin layer chromatography.

STATEMENT OF UTILITY

The compounds of formula I of this invention are useful as pharmaceutical agents in animals. In particular, the compounds of the formula I are useful as antiatherosclerotic agents, i.e. agents useful in the prophylactic treatment of atherosclerosis and in the controlling of atherosclerotic conditions due to cholesterol ester accumulation in the arterial walls. Such ability of the compounds of the formula I is indicated e.g., by known test procedures in which the total cholesterol ester content of cultured cells is shown to be reduced by a test compound, as compared to untreated cells, and carried out, for example, by the following procedures:

(A) Cell culture

Fu5AH rat hepatoma cells (Rothblat, G. M., Lipids 9, 526–535; 1974) are routinely grown in 75 cm² tissue culture flasks using Minimum Essential Medium (Eagle) supplemented with 10% fetal bovine serum. For testing a 75 cm² flask with a near confluent cell growth is selected. The cells are removed from the flask surface by mild enzymatic treatment with pronase. After centrifugation and decanting the enzyme solution, the cell pellet is resuspended in an appropriate volume of media for seeding the desired number of 60 mm tissue culture dishes. Five (5) ml of the diluted cell suspension are pipetted into each dish. After seeding, the dishes are labelled with the cell type, date and flask number of origin and incubated at 37° C. in approximately 5% $CO_2$ atmosphere in a high humidity incubator. When the cultures are confluent, the actual drug testing is begun. Test compounds are routinely solubilized in 100% ethanol. An equivalent amount of ethanol is added to control groups as well. The tissue culture dishes are randomly divided into groups. To one group, hyperlipemic rabbit serum (HRS) is addded at 5% by volume (control). To the remaining groups, 5% HRS and 0.1 mg to 1 mg per 100 ml of media of the test compound are added. The dishes are returned to the incubator for an additional 24 hours. All operations through to the final incubation are performed using sterile technique in a laminar flow hood. After the incubation period, the dishes are microscopically observed with the Zeiss Axiomat with phase contrast optics and the conditions of the cultures are recorded; especially in regard to the shape, size, number and configuration of cytoplasmic lipid inclusions. A qualitative assessment of inclusions in test compound-treated group relative to control and standard is made, re, (1) no drug effect;
(2) reduced number of inclusions $<$, $=$, $>$ standard.

The standard is ($\pm$) 4,4-dimethyl 4-sila-tetradecanoyl-1'-phenyl-2'-p-tolyl-ethylamide reported in the literature, e.g. European Patent No. 12,183*. A reduction in the number and size etc. of the inclusions indicates a reduction in cholesterol ester accumulation. Alternatively, $\alpha$-(1-oxo-9-octadecenylamino)-1H-indole-3-propionic acid, ethyl ester (cis isomer)** may be used as standard, preparation of which is disclosed in Belgian Patent No. 873,365 (Derwent 50,885B) and British Pat. No. 2,012,261A.

*Derwent 46,562 C (1980), also obtainable by the methods described in U.S. Pat. No. 4,297,349.
**Also called N-(1-oxo-9-octadecenyl)-D,L-tryptophan-(Z), ethyl ester or N-oleyl O-ethyl D,L-tryptophan.

The antiatherosclerotic effective dosage of active ingredient employed for the reduction of cholesterol ester content in the arterial walls of a mammal may vary depending on the particular compound employed, the mode of administration and the severity of the condition being treated. However, in general, satisfactory results are obtained when the compounds of formula I are administered at a daily dosage of from about 0.2 milligrams to about 500 milligrams per kilogram of animal body weight, preferably given in divided doses two to four times a day, or in sustained release form. For most large mammals, the total daily dosage is from about 500 mg. to 15,000 mg., preferably from about 1000 mg. to 5,000 mg. Dosage forms suitable for internal use comprise from about 250 mg. to 7,500 mg. e.g., from about 250 mg. to 2,500 mg. of the active compound in intimate admixture with a solid or liquid pharmaceutically acceptable carrier. Solid carriers include starch, lactose and kaolin, while liquid carriers include sterile water, polyethylene glycols and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants e.g. vitamin E, ascorbic acid, BHT and BHA.

The compounds are preferably administered orally. The preferred pharmaceutical compositions from the standpoint of ease of preparation and administration are solid compositions for oral administration, particularly tablets and hard-filled or liquid-filled capsules.

Where the final product (I) is waxy or oily and oral dosages in the higher ranges are desired, the product may conveniently be administered in an aqueous suspension; the flavor thereof being enhanced by fruit flavors and the like, e.g., as a "milk shake" or "cocktail", by methods well known in the art, e.g., using CMC as a suspending agent.

When the compounds I are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

Representative formulations for administration orally three times a day prior to feeding in the treatment of atherosclerosis is a gelatin capsule prepared by conventional techniques to contain the following

| Ingredient | Weight (in Mg.) | |
| --- | --- | --- |
| N—5-Sila-3-thia-5,5-dimethyl-pentadecanoyl-1-phenyl-2-(4-methyl phenyl)-ethylamine | 300 | 500 |
| Lactose | 200 | — |

While the inventor does not wish to be bound by any proposed theory of the mechanism of the action of Compounds I, it has been observed in tests on analogous compounds using the Zilbersmit Dual Isotope Method* that such compounds substantially reduce absorption of cholesterol from the gastro-intestinal system of the host, i.e. at the intestinal wall, possibly by action involving the Acyl Coenzyme A cholesterol acyl transferase (ACAT) enzyme, resulting in a marked reduction of cholesterol intake into the blood of the host, as well as a reduction in the cholesterol content (in free and as ester form) of smooth muscle cells of the host, e.g. arterial walls, such as those of the aorta and coronary arteries, thus minimizing or avoiding plaque formation therein.

*Described in Proc. Soc. Exp. Biol. Med. 140: 862–865 (1972)

Employing the above-described cell culture test method (using Fu5AH cells) and as test compound* the product of Example 1, below, marked activity is observed at the 0.1 mg and 1 mg. levels.

*using $\alpha$-(1-oxo-9-octadecenylamino)-1H-indole-3-propionic acid, ethyl ester (cis isomer) as standard.

The following examples of the preparation of intermediates and final compounds (I) of the invention are illustrative of the invention. All temperatures are centigrade (°C.) and room temperature is 20° to 30° C., unless indicated otherwise.

It will be appreciated that the products of these examples may exist in the form of stereoisomers, e.g. optically active isomers, although, e.g. ($\pm$) racemic mixtures or a particular form are specifically mentioned.

EXAMPLE 1

N-5-Sila-3-thia-5,5-dimethyl-pentadecanoyl-1-phenyl-2-(4-methylphenyl)-ethylamine

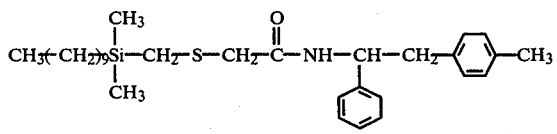

Step A 5-Sila-3-thia-5,5-dimethyl-pentadecanoic acid

A solution of 25.4 g (74.7 mmol) of decyl-dimethyl-iodomethylsilane in 100 ml of absolute (distilled from CaH$_2$) N,N-dimethylformamide containing 10.0 g (87.6 mmol) of mercaptoacetic acid sodium salt is refluxed for 5 hr. The cooled mixture is distributed between cold water and hexane. The hexane layer is washed with three portions of water, dried (anh. sodium sulfate), filtered and concentrated to crude oily product of this step. The oil is filtered through silica gel in dichloromethane solution, followed by elution with 6% methanol in chloroform. Concentration of this eluate yields refined product, which is further refined by Kugelrohr distillation, to obtain a main cut at 125°–140°/133–90 micron pressure.

Step B
N-5-Sila-3-thia-5,5-dimethyl-pentadecanoyl-1-phenyl-2-(4-methylphenyl)-ethylamine.

A solution of 4.0 g (13.15 mmol) of the acid obtained in step A and 0.05 ml, (0.65 mmol) of N,N-dimethylformamide (catalyst) in 30 ml dry toluene plus 30 ml absolute (distilled from LiAlH$_4$) tetrahydrofuran is stirred at −30° to −40°, under dry nitrogen, while 1.1 ml (1.82 g, 15.3 mmol) of thionyl chloride is cautiously added. The resultant solution is further stirred while it is allowed to warm to 0° in 15 min., 20° in 45 min. It is then concentrated in vacuo with protection from moisture to obtain a residue (corresponding acid chloride). The residue is dissolved in a fresh portion of dry toluene-THF.

During this time 3.4 g (13.7 mmol) of the hydrochloride of 1-phenyl-2-(p-methylphenyl)ethylamine in dichloromethane is mixed with an excess of aqueous sodium hydroxide, to liberate the free base. The dichloromethane solution is dried (over anh. sodium sulfate) and concentrated to obtain the base, which is mixed with 2.0 ml of triethylamine and added to the solution of the acid chloride at from 0° to −20°. The resultant slurry is stirred for 16 hr. at 20°. It is then distributed between water and diethyl ether. The ether phase is combined with toluene after removal of the ether solvent. The organic solution is washed with three portions of dilute hydrochloric acid, three portions of sodium bicarbonate (aq. solution), dried over anh. sodium sulfate, filtered and concentrated to oily crude product. The oil is chromatographed on silica gel, eluting with 4% isopropanol in dichloromethane. Concentration of the main cut gave product which is evaporatively distilled at up to 130° at 110 micron pressure, resulting in 4.8 g of microanalytically pure product of this example.

EXAMPLE 2

Repeating the procedure of Example 1, but using in place of the 1-phenyl-2-(p-methylphenyl)ethylamine used therein, an approximately equivalent amount of the following amines as compounds II:
(a) 1-amino-indane;
(b) DL-tryptophan ethyl ester, hydrochloride;*
(c) (d,l) α-methylbenzylamine;
(d) 2-methylaniline; or
(e) 1′-benzyl-2′-phenylethylamine
there is accordingly obtained, respectively (Compounds I):
(a) N-5-sila-3-thia-5,5-dimethyl-pentadecanoyl-1-indanylamine;
(b) N-5-sila-3-thia-5,5-dimethyl-pentadecanoyl-tryptophan, ethyl ester;
(c) N-5-sila-3-thia-5,5-dimethyl-pentadecanoyl-α-methylbenzylamine;
(d) N-5-sila-3-thia-5,5-dimethyl-pentadecanoyl-o-methylphenylamine; and
(e) N-5-sila-3-thia-5,5-dimethyl-pentadecanoyl-1′-benzyl(2′-phenyl)ethylamine;

*an additional equivalent of the acid binding agent (triethylamine) is used.

EXAMPLE 3

Repeating the procedure of step A of Example 1, but in place of the n-decyl-dimethyl-iodosilane, used therein, using an approximately equivalent amount of the following iodides (as compounds VII):
(a) n-butyl-dimethyl-iodomethylsilane;
(b) trimethyl-iodomethylsilane;
(c) phenyl-dimethyl-iodomethylsilane;
(d) benzyl-dimethyl-iodomethylsilane;
(e) n-butyl-diphenyl-iodomethylsilane; or
(f) n-octyl-dimethyl-3-iodo-propylsilane;
There is accordingly obtained, respectively, the following acids (Compounds V):
(a) 5-sila-3-thia-5,5-dimethyl-n-nonanoic acid;
(b) 5-sila-3-thia-5,5-dimethyl-n-hexanoic acid;
(c) 5-sila-3-thia-5,5-dimethyl-5-phenyl-pentanoic acid;
(d) 5-sila-3-thia-5,5-dimethyl-6-phenyl-hexanoic acid;
(e) 5-sila-3-thia,5,5-diphenyl-n-nananoic acid; and
(f) 7-sila-3-thia-7,7-dimethyl-n-pentadecanoic acid;
which when used in the manner of Step B of Example 1, in an approximately equivalent amount in place of the 5-sila-3-thia-5,5-dimethyl-pentadecanoic acid, used therein, there is accordingly obtained, respectively, each of the corresponding amides of 1-phenyl-2-(4-methylphenyl)ethylamine thereof.

EXAMPLE 4

Repeating the procedure of Step A of Example 1, but using in place of the mercaptoacetic acid, used therein, an approximately equivalent amount of 3-mercaptopropionic acid (as a compound VIII), there is accordingly obtained 6-sila-4-thia-6,6-dimethyl-n-hexadecanoic acid, which when used in Step B in place of the 5-sila-3-thia-5,5-dimethyl-pentadecanoic acid used therein, there is accordingly obtained N-6-sila-4-thia-6,6-dimethyl-hexadecanoyl-1-phenyl-2-(4-methyl-phenyl)-ethylamine.

What is claimed is:
1. A compound of the formula:

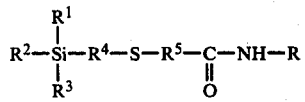

wherein each of
R$^1$, R$^2$ and R$^3$ is, independently, alkyl having from 1 to 22 carbon atoms, alkenyl having from 2 to 22 carbon atoms, cycloalkyl having from 3 to 20 ring carbon atoms, aryl having from 6 to 14 aromatic ring carbon atoms, or aralkyl having from 6 to 14 aromatic ring carbon atoms and from 1 to 4 carbon atoms in the alkylene portion thereof; or
R$^2$ and R$^3$ may be joined to form together with the silicon atom a saturated sila-hydrocarbyl ring having from 4 to 20 ring members,
provided that the total number of carbon atoms in R$^1$+R$^2$+R$^3$, other than aromatic ring carbon atoms or substituents thereon, is not more than 35, each of $R^4$ and $R^5$ is, independently, an alkylene chain having from 1 to 6 carbon atoms, or a cycloalkylene radical having from 3 to 6 ring carbon atoms; said cycloalkyl and cycloalkylene radicals may bear from 1 to 4 lower alkyl groups having from 1 to 6 carbon atoms; said aryl radicals, or portions thereof, may bear 1 or 2 halo substituents, each having an atomic weight of from about 19 to 80, or from 1 to 3 lower alkyl or alkoxy radicals each having from 1 to 6 carbon atoms; and R is of type (a) an aralkyl-type radical of the structure

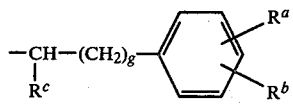 (a)

wherein
g is 0, 1 or 2;
$R^a$ is a hydrogen atom, halo having an atomic weight of from about 19 to 127, alkoxy having from 1 to 4 carbon atoms, or alkyl having from 1 to 4 carbon atoms, or trifluoromethyl;
$R^b$ is a hydrogen atom, alkyl having from 1 to 3 carbon atoms, alkoxy having from 1 to 3 carbon atoms, or halo having an atomic weight of from about 19 to 36; and
$R^c$ is subtype (i) a hydrogen atom; subtype (ii) a radical of the structure

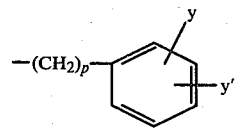 (ii)

in which
p is 0, 1 or 2, and
y is a hydrogen atom, halo having an atomic weight of from about 19 to 127, alkoxy having from 1 to 4 carbon atoms, or alkyl having from 1 to 4 carbon atoms; and
y' is a hydrogen atom, alkoxy having from 1 to 3 carbon atoms, alkyl having from 1 to 3 carbon atoms, or halo having an atomic weight of from about 19 to 36; or
subtype (iii) alkyl having from 1 to 8 carbon atoms; or
R is of type (b) a phenyl-type radical of the structure

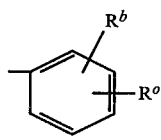 (b)

in which
$R^b$ is as defined above, and
$R^o$ is a hydrogen atom, halo having an atomic weight of from about 19 to 127, alkoxy having from 1 to 4 carbon atoms, or alkyl having from 1 to 4 carbon atoms; or
$R^o$ is a radical of the structure $R^f$:

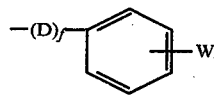

in which
D is —$CH_2$— or —O—;
f is 0 or 1; and
W is a hydrogen atom, halo having an atomic weight of from about 19 to 80, alkoxy having from 1 to 3 carbon atoms, or alkyl having from 1 to 3 carbon atoms; or R is of type (c) an indolyl radical of the structure:

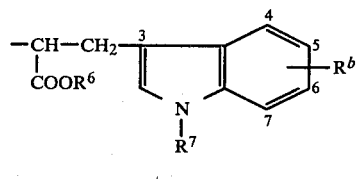 (c)

wherein
$R^b$ is as defined above;
$R^6$ is alkyl having from 1 to 8 carbon atoms or benzyl; and
$R^7$ is a hydrogen atom, alkyl having from 1 to 8 carbon atoms or benzyl; or R is (d) a benzocycloalkyl nucleus of the structure:

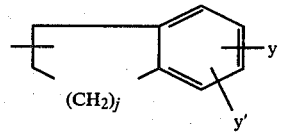 (d)

wherein
y and y' are as defined above; and
j is a whole integer of from 1 to 4.

2. A compound of claim 1 in which R is of type (a)
3. A compound of claim 1 in which R is of type (b)
4. A compound of claim 1 in which R is of type (c)
5. A compound of claim 1 in which R is of type (d)
6. A compound of claim 1 in which $R^2$ and $R^3$ are lower alkyl having from 1 to 4 carbon atoms.
7. A compound of claim 6 in which $R^2$ and $R^3$ are the same.
8. A compound of claim 7 in which $R^2$ and $R^3$ are methyl.
9. A compound of claim 1 in which each of $R^4$ and $R^5$ is methylene.
10. The compound of claim 1 which is N-5-sila-3-thia-5,5-dimethyl-pentadecanoyl-1-phenyl-2-(4-methylphenyl)-ethylamine.
11. A method of inhibiting the accumulation of cholesterol ester in an arterial wall of a mammal in need of such treatment, comprising administering a cholesterol ester-inhibiting amount of a compound of claim 1 to said mammal.
12. A pharmaceutical composition suitable for inhibiting the accumulation of cholesterol ester in arterial wall of a mammal comprising a cholesterol ester-inhibiting-effective amount of a compound of claim 1 and a non-toxic pharmaceutically-acceptable carrier.
13. A composition of claim 12 in solid form.
14. A composition of claim 12, in which the compound is present in an amount of from about 250 to 7,500 milligrams.
15. A method of claim 11 in which the daily dose of the compound is from about 500 mg to 15,000 mg.

* * * * *